United States Patent [19]

Korn

[11] Patent Number: 5,067,896
[45] Date of Patent: Nov. 26, 1991

[54] ORTHODONTIC APPLIANCE

[76] Inventor: Marcel Korn, 328 Newberry St., Boston, Mass. 02115

[21] Appl. No.: 690,594

[22] Filed: Apr. 24, 1991

[51] Int. Cl.$^5$ .............................................. A61C 3/00
[52] U.S. Cl. .......................................... 433/6; 433/24
[58] Field of Search .................. 433/6, 18, 24, 37, 48; 128/859, 861, 862

[56] References Cited

U.S. PATENT DOCUMENTS 3,224,441 12/1965 Monaghan .
3,379,193 4/1968 Monaghan .
4,063,552 12/1977 Going et al. .
4,073,061 2/1978 Bergersen .

Primary Examiner—Cary E. O'Connor
Attorney, Agent, or Firm—Lloyd L. Zickert

[57] ABSTRACT

A custom-made resilient orthodontic appliance for positively positioning the opposing arches relative to each other and a method for making the appliance, wherein the appliance includes a body of thermoplastic material sized to have impressions of the upper and lower anterior teeth and including means for connecting the appliance to one of the arches when it is worn by a patient. The method of making the appliance is such that it can be made at chairside by taking an arcuately shaped blank of material, heating the material so that it is softened, placing it in the patient's mouth and adjusting the desired relative positions of the arches, having the patient close his jaws on the blank to form an impression of the anterior teeth in the blank, allowing the blank to remain in the mouth until it is in an initially set condition, and then removing the blank from the mouth and subjecting it to additional cooling to permanently set the impression in the blank. Thereafter, the appliance may be worn by the patient by connecting it to one of the arches such as by use of elastic ligatures hooked over the appliance and fixed appliances on adjacent teeth.

14 Claims, 2 Drawing Sheets

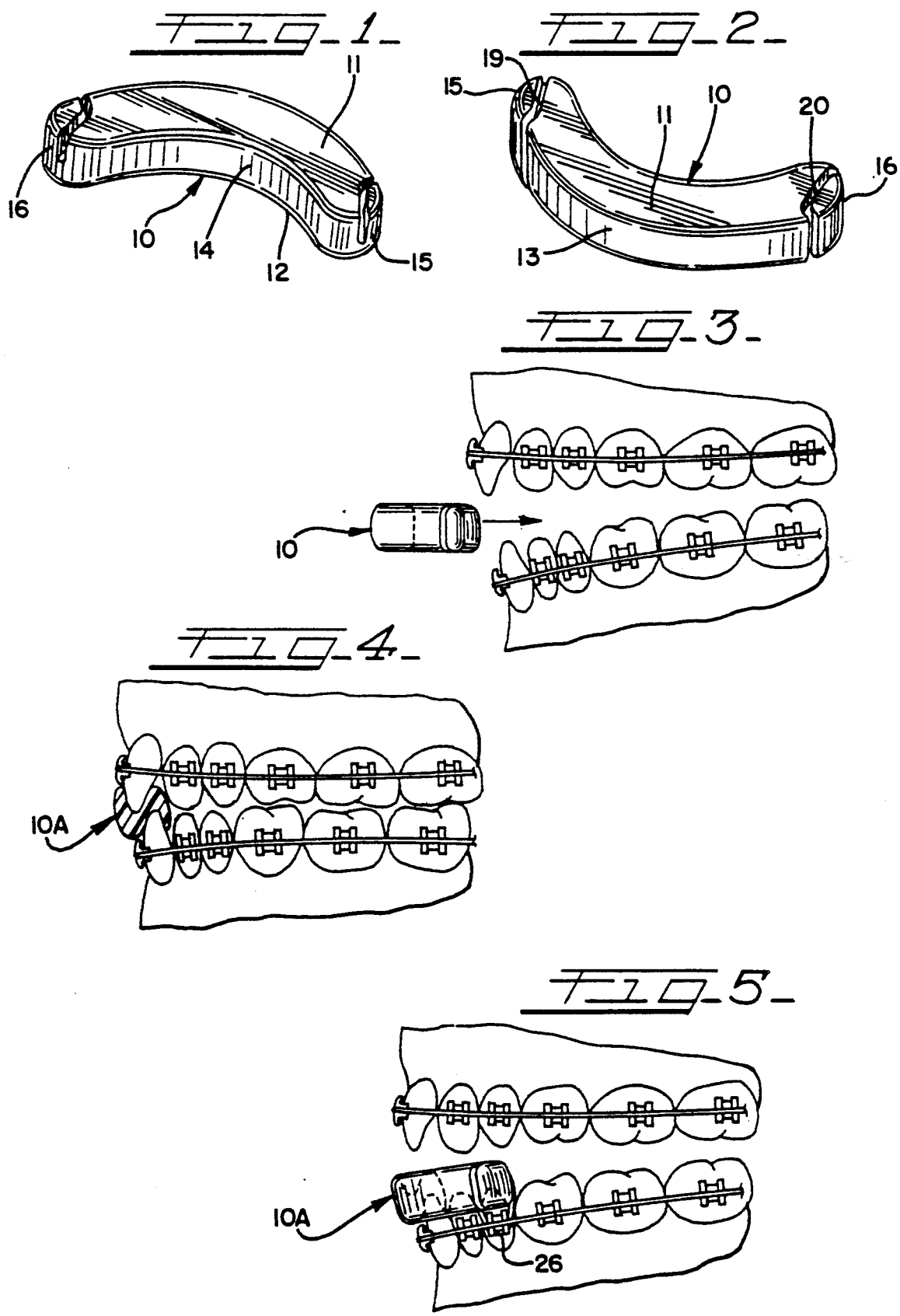

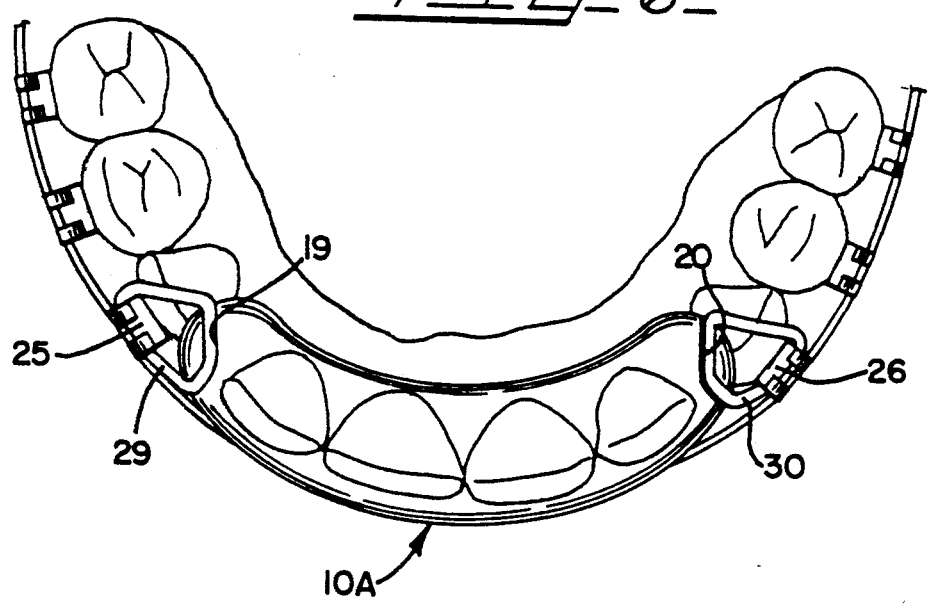
FIG_6_
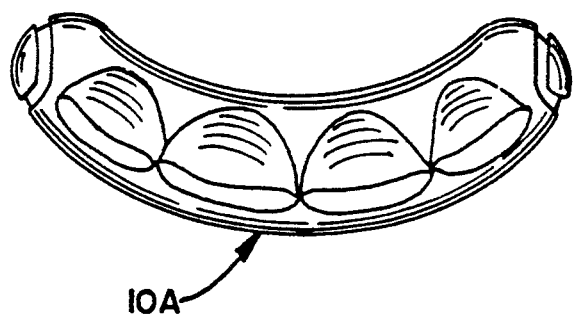
FIG_7_
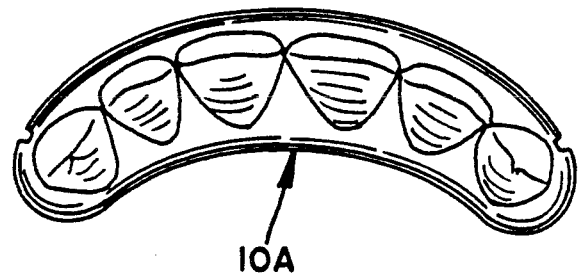
FIG_8_
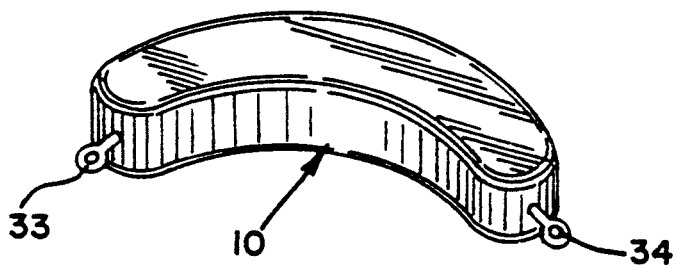
FIG_9_

ORTHODONTIC APPLIANCE

DESCRIPTION

This invention relates in general to a custom-made resilient orthodontic appliance for functioning as a jaw-positioning device and a method of making the appliance, and more particularly to an appliance made of material that can be provided with an impression of the anterior teeth of the patient by the patient through simple chairside procedures by the orthodontist.

BACKGROUND OF THE INVENTION

Heretofore, orthodontic appliances have been provided for patients for purposes of facilitating the positioning or alignment of opposing dental arches which have generally required laboratory procedures for making the appliance between visits by a patient. Some appliances have been rather complex in structure and relatively expensive to make.

It has been known to make appliances for wearing by persons that are in the form of mouthguards or teeth protectors which are constructed from blanks of thermoplastic material that may be softened by heating so as to allow impressions of teeth to be formed in the blanks, and where the mouthguard is worn for purposes of protecting the teeth particularly where the wearer is involved in athletics. Such mouthguards, however, are not intended to serve as jaw-positioning devices, and are not intended to be worn in conjunction with fixed orthodontic appliances for the purpose of orthodontically treating a person and for obtaining a correction of the relation between dental arches.

SUMMARY OF THE INVENTION

The orthodontic appliance of the present invention is a custom-made jaw-positioning device that is made through simple chairside procedures by the orthodontist, thereby eliminating the need for any laboratory procedures to make the appliance. Thus, the appliance may be made when needed by the orthodontist when the patient comes in for an appointment. The present invention not only relates to the appliance but also to the method of making the appliance which enhances the usefulness of the appliance.

The appliance is in the form of an arcuate body having an impression of the anterior teeth prescriptively positioned in accordance with a clinical analysis. When worn by the patient it is releasably connected to one arch such as by the use of elastic ligatures that hook over the appliance and over fixed appliances on adjacent teeth. Thus, the appliance is to be used during fixed appliance therapy, that is, in conjunction with orthodontic braces already affixed to the patient's teeth. It may be readily adapted to an individual patient's requirements with a minimum of effort by the orthodontist. Further, it is removable and attachable by the patient.

The appliance is made by using an arcuately shaped wafer or blank of a thermoplastic polymer which is heated until it is in a softened state so that it can take the impression of teeth. After it is softened, the orthodontist places it between the anterior teeth and onto the anterior segment of either arch. The patient is then brought into the desired jaw relationship by the orthodontist and the arches are closed in a controlled manner to form the impression of the anterior teeth. After a short period of time, the material sets and the appliance is removed from the mouth and further cooled in an appropriate manner so that the final form is set. Thereafter, the appliance can be attached to one of the arches by use of elastic ligatures or the like, and this may be accomplished by the patient upon receiving proper instructions.

Inasmuch as the appliance is connected to only one arch, the jaws may be separated so the patient can talk, and thereafter the patient can bring the jaws together again into the teeth sockets of the appliance to carry on the orthodontic treatment for which the appliance is intended to accomplish.

It is therefore an object of the present invention to provide a new and improved orthodontic appliance and method of making same wherein the appliance is used as a jaw-positioning device.

Another object of the invention is in the provision of an improved appliance and method of making the same where the appliance is useful for orthodontic treatment of a patient having fixed appliances and where the appliance may be custom made by the orthodontist through simple chairside procedures and wherein the appliance may be made at a low cost and which requires a minimal inventory of product by the orthodontist.

A still further object of the invention is to provide an improved jaw-positioning device for orthodontically treating patients which is compatible with fixed appliance therapy and readily adaptable to the varied anatomy of patients.

Another object of the invention is in the provision of a custom-made orthodontic appliance to function as a jaw-positioning device and which can be made by the orthodontist through chairside procedures, thereby eliminating any need for laboratory procedures.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a top perspective view of a blank of thermoplastic material for making the custom orthodontic appliance of the present invention and looking at the blank from the lingual side;

FIG. 2 is a perspective view like FIG. 1 but looking at the blank from the labial side, which is a reversed position from that shown in FIG. 1;

FIG. 3 illustrates the step of inserting a softened blank of thermoplastic material into the mouth of a patient by showing upper and lower arches with fixed appliances in open position and the manner in which the blank will be brought into engagement with the teeth of one arch prior to making an impression of the anterior teeth in the blank;

FIG. 4 is a view similar to FIG. 3 but illustrating the teeth in closed position on the blank in cross section in order to form the impression of the teeth and wherein the appliance is illustrated in vertical section to show the relationship of the teeth and also illustrating the manner in which the completely formed appliance is worn by the patient;

FIG. 5 is a view of the arches in open position and with the completely formed appliance attached to the mandibular jaw;

FIG. 6 is a top plan view of the mandibular jaw or lower arch with the appliance in place on the lower anterior teeth and illustrating the manner in which elastic ligatures are utilized for releasably attaching the appliance to the lower arch;

FIG. 7 is a top plan view of the completed appliance which has been custom fitted for a patient and illustrating the appliance having the impressions of the front four anterior teeth that include the centrals and the laterals;

FIG. 8 is a bottom plan view of the appliance of FIG. 7 and showing that the bottom six teeth have made an impression in the underside of the blank which include the centrals, laterals and canines; and FIG. 9 is a perspective view like FIG. 1 showing a blank of thermoplastic material that has a modified means for attaching the blank to the teeth in the form of eyelets extending from the opposite ends of the appliance.

DESCRIPTION OF THE INVENTION

The custom-made jaw-positioning device of the present invention is made of a resilient thermoplastic material and for fitting on the anteriors of the upper and lower arches. Typically, the appliance will be sized so that it will carry the sockets of the upper front four teeth including the centrals and laterals and the lower six teeth including the centrals, laterals and canines. However, the appliance could be made to receive additionally the upper canines if so desired. For purposes of being an acceptable jaw-positioning device, the appliance need only have sockets for the upper four teeth and the lower six teeth. It should also be appreciated that the appliance may be made to accommodate even a smaller number of teeth of both arches.

The thermoplastic material used for making the appliance is a material sold under the trademark Elvax by DuPont and which softens at about 150 degrees F. and has a hardness of about 85 Shore A. It is important to have a material that can be placed into the patient's mouth without causing undue comfort due to its temperature during the impression-making step.

While the orthodontic appliance of the invention may be used for any number of treatment plans, it may, for example, be used for Class II correction of mandibular retrognathism, vertical correction of deep overbite cases, facilitation of tooth movement by elimination of tooth-to-tooth interferences, and anchorage control of the anterior arch segments needed in specific treatment sequences.

The appliance may also be used in temporomandibular unction (TMJ) therapy. For example, it may be used as a diagnostic appliance to function as a diversion from a TMJ condition. It may also be used as an immediate splint for diagnosis or treatment of acute TMJ cases. Further, it may be used as a stabilizer or retentive appliance for repostured patients Finally, it may be used as a isometric exerciser for patients with decreased bite opening.

The appliance of the invention may also be used as a retainer for mandibular advancement cases following orthognathic surgery.

Referring now to the drawings, and particularly to FIGS. 1 and 2, the custom-fitted orthodontic appliance of the invention is made from a blank or wafer 10 of thermoplastic material which is formable when softened by heat. The blank 10 is arcuately shaped and includes upper and lower substantially flat surfaces 11 and 12, a front or labial curved wall or surface 13 that is convex, and a rear or lingual wall or surface 14 that is concave.

Rounded ends 15 and 16 interconnect the front and back walls 13 and 14. A cross section through the wafer will be substantially rectangular. The actual shape may be otherwise, but it must match the alignment of the anteriors, and it is preferable to have upper and lower substantially flat surfaces into which the impression can be made.

With respect to the embodiment of FIGS. 1 and 2, ligature slots or grooves 19 and 20 are formed at opposite ends of the blank wherein the slots include a segment through the upper surface 11 and a segment through the front wall or surface 13. The slot serves to receive an elastic ligature when the appliance is made and for releasably attaching the appliance to one of the dental arches, as will be hereinafter more specifically described.

Thus, the blank is of substantially solid thermoplastic material and which may be easily softened in the environment of a heated liquid, such as water, or heated air, so that a suitable impression of the teeth can be made in the blank.

The procedure for making the appliance is relatively simple and can be made through chairside procedures. The orthodontist or clinician would select a desired blank of thermoplastic material for making the appliance. It can be appreciated that the thickness of the blank will be such that it will accommodate the impression of the upper and lower anterior teeth, as illustrated in FIG. 4. The length of the blank will be such that it will preferably receive the impression of the upper front four teeth and the lower front six teeth, as illustrated in FIGS. 7 and 8, although it could be sized to receive a lesser or slightly greater number of teeth if desired. It has been found that when it is used for the anterior teeth which include the upper centrals and laterals and the lower centrals, laterals and canines, the appliance will provide the desired jaw-positioning functions when treating a patient.

After selecting the desired blank, the orthodontist would soften the material of the blank such as by placing it in water of a temperature that will accomplish the softening or by placing it in a heated environment that would accomplish the softening. After the blank has been suitably softened, the orthodontist would engage it with a suitable instrument and place it on the teeth of a patient in readiness for making the impression. Thus, the blank would be aligned with one of the arches such as by placing it on the lower arch, and the mandibular jaw would be positioned relative to the maxillary jaw to the desired position, and the jaws would be closed in a controlled manner to form the impression in the blank of the upper and lower anterior teeth. When closed to the desired position, the patient will be instructed to maintain that position for a short period of time until the plastic blank has set up with the impression. After the plastic has initially set, it will be removed from the mouth of the patient by the orthodontist and subjected to a further cooling, such as being placed into cold water or an environment where cold air is presented. This will completely set the appliance with the tooth sockets of the upper and lower teeth custom fitted to the teeth of the patient.

Thereafter, the orthodontist would instruct the patient on how to use the appliance. Where the appliance is to be releasably attached to the lower arch, the orthodontist would place the appliance on the lower anterior teeth and show the patient how to attach the teeth to the fixed appliances by use of elastic ligatures.

It will be appreciated that the appliance of the invention will be used on a patient undergoing fixed appliance therapy where braces would be mounted on the upper and lower teeth. This would be the normal way of using the appliance although it could be used at other stages of orthodontic treatment. Whenever it is used, it is necessary to have a fixed appliance mounted on certain teeth for the purpose of hooking an elastic ligature at each end of the appliance and over adjacent fixed appliances. For example, it can be seen in FIGS. 3, 4, 5 and 6 that fixed appliances 10A are mounted on the upper and lower dental arches. These fixed appliances are in the form of orthodontic brackets for receiving an archwire, as illustrated in FIGS. 5 and 6. When the appliance 10A is properly positioned on the lower arch, the ends will be adjacent to the first bicuspids. As seen particularly in FIG. 6, these first bicuspids have twin-wing brackets 25 and 26 mounted on their buccal faces. Elastic ligatures 29 and 30 are provided at opposite ends of the appliance for engaging in the slots 19 and 20 and for also hooking over the tie wings of brackets 25 and 26. The elastic ligatures will suitably connect the appliance to the lower arch whereby the upper anterior teeth may be engaged in the upper sockets of the appliance and thereafter released from the upper sockets without causing removal of the appliance. Thus, the patient can open his mouth from time to time, such as for purposes of talking.

A modified means for connecting the appliance to a dental arch is shown in FIG. 9 wherein metal eyelets 33 and 34 are suitably anchored in the ends of the blank 10 in place of slotting the ends as in the embodiment in FIGS. 1 and 2. The eyelets may even be in the form of hooks if so desired so as to receive a ligature that can thereafter be tied to the brackets.

It will be appreciated that the appliance will be retained in the mouth by the ligatures connecting it to an arch, giving the appliance stability and repeatability of engagement and disengagement between the upper anterior teeth and the appliance. In place of brackets, it may be appreciated that buttons may be mounted on the teeth for receiving a ligature that will attach the appliance to the teeth. It may be also appreciated that the appliance may be connected to the upper arch instead of the lower arch if desired.

In view of the foregoing, it will be appreciated that the appliance and method of making the appliance according to the invention is simple to make through chairside procedures by the clinician without the need of undergoing laboratory procedures. The cost of making the appliance is relatively low since no laboratory procedures are necessary and only a minimal inventory of blanks or wafers will need to be maintained by the orthodontist. As above mentioned, the appliance can serve to assist in the treatment of patients in any number of situations. After the patient is fitted with the appliance, if the patient does not wear it for a period of time in which the alignment of the teeth would change, the appliance when worn thereafter can additionally serve to reposition the teeth into the alignment at the time the appliance was made.

It will be understood that modifications and variations may be effected without departing from the scope of the novel concepts of the present invention, but it is understood that this application is to be limited only by the scope of the appended claims.

The invention is hereby claimed as follows:

1. A method of making a custom-fitted resilient orthodontic appliance for attachment to the anterior of the mandibular arch or the maxillary arch anteriors and coacting with the opposed anteriors when the jaws are in closed position to positively position the opposing dental arches relative to each other, said method comprising the steps of providing an arcuately shaped plastic blank having a generally rectangular cross section and means at the ends for assisting the attachment to one of the arches, said blank having upper and lower substantially flat surfaces and being of a thermoplastic material that is formable when softened by heat and resilient when at normal room and mouth temperatures, heating the blank to soften it to facilitate the impression of tooth sockets in the upper and lower surfaces of the blank, placing the softened blank in the mouth of a patient so that the upper and lower teeth can engage the upper and lower surfaces of the blank, closing the jaws of the patient into the desired jaw relationship to form an impression of the teeth and define tooth sockets for the upper and lower anterior teeth in the upper and lower sides of the blank, allowing the blank to remain in the mouth under pressure of the teeth until the impression of the teeth is set in the blank, removing the formed blank from the patient's mouth, and further cooling the blank so that the impression of the teeth is completely set and the blank is transformed into an appliance for positively positioning the jaws completely relative to each other when the appliance is worn by the patient.

2. The method of claim 1, wherein the blank is sized for receiving an impression of the centrals and laterals.

3. The method of claim 1, wherein the blank is sized for receiving an impression of the centrals, laterals and canines.

4. The method of claim 1, wherein the means for attachment includes grooves or slots for receiving elastic ligatures that may be connected to fixed appliances on the teeth.

5. The method of claim 4, wherein the grooves or slots are formed so that the appliance may be attached to the mandibular arch by hooking elastic ligatures on the groove or slot ends of the appliance and over adjacent fixed appliances on the lower teeth.

6. The method of claim 1, wherein the means for attachment includes one or more eyelets for receiving ligatures that connect to fixed appliances on the teeth.

7. The method of claim 1, wherein the material for the appliance is such that it will maintain positive indentations for teeth and adjacent structures, while permitting the patient to readily release his teeth from the appliance.

8. The method of claim 1, wherein the material has a hardness of about 85 Shore A and softens at about 150 degrees F.

9. An orthodontic appliance made in accordance with the method of claim 8.

10. An orthodontic appliance made in accordance with the method of claim 1.

11. A custom-made resilient orthodontic appliance attachable to one of the arches for positively positioning the opposing dental arches relative to each other, said appliance comprising an arcuately shaped body having tooth sockets of the upper and lower anterior teeth formed in the body such that when the appliance is worn and the teeth are received in the sockets, the opposing arches will be disposed relative to each other according to a desired position diagnosed by the treating orthodontist, and means on the ends of the appliance for coacting with ligatures to attach the appliance to one arch.

12. The appliance of claim 11, wherein the attaching means includes grooves formed in the appliance for receiving ligatures that may be hooked onto fixed appliances mounted on adjacent teeth.

13. The appliance of claim 12, wherein the ligatures are elastics.

14. The appliance of claim 11, wherein the attaching means includes eyelets for receiving ligatures that may be connected to fixed appliances on adjacent teeth.

* * * * *